United States Patent [19]

Cines

[11] 4,053,369
[45] Oct. 11, 1977

[54] EXTRACTIVE DISTILLATION

[75] Inventor: Martin R. Cines, Bartlesville, Okla.

[73] Assignee: Phillips Petroleum Company, Bartlesville, Okla.

[21] Appl. No.: 744,857

[22] Filed: Nov. 24, 1976

Related U.S. Application Data

[63] Continuation of Ser. No. 474,498, May 30, 1974, abandoned.

[51] Int. Cl.$^2$ ............................................. B01D 3/34
[52] U.S. Cl. ........................................ 203/52; 203/54; 203/55; 203/56; 203/58; 203/62; 203/64; 203/65; 203/66; 208/358; 260/674 A; 260/674 N; 260/676 R; 260/677 A; 260/681.5 R
[58] Field of Search ....................... 203/43, 44, 46, 57, 203/58, 62, 64, 65, 66, 52–56; 208/347, 350, 358; 260/674 R, 674 A, 674 N, 674 SE, 676 R, 677 R, 677 A, 681.5 R

[56] References Cited

U.S. PATENT DOCUMENTS

| | | | |
|---|---|---|---|
| 2,243,873 | 6/1941 | Lyman | 260/674 |
| 2,257,283 | 9/1941 | Snow | 208/313 |
| 2,325,379 | 7/1943 | Durrum | 203/57 |
| 2,416,724 | 3/1947 | Whaley | 261/114 |
| 2,501,114 | 3/1950 | Whaley | 261/18 |
| 3,216,929 | 10/1961 | Favre | 208/312 |
| 3,235,471 | 2/1966 | Clay | 203/54 |
| 3,338,824 | 8/1967 | Oliver | 137/82 |
| 3,366,568 | 1/1968 | Eisenlohr et al. | 208/313 |
| 3,372,109 | 3/1968 | Davis et al. | 208/373 |
| 3,396,101 | 8/1968 | Broughton | 208/313 |
| 3,527,837 | 9/1970 | Woerner et al. | 260/683.3 |
| 3,679,579 | 7/1972 | Preusser et al. | 208/323 |
| 3,702,295 | 11/1972 | Thompson | 208/321 |
| 3,723,256 | 3/1973 | Thompson | 203/43 |
| Re. 26,255 | 8/1967 | Papadopoulous et al. | 208/313 |

FOREIGN PATENT DOCUMENTS

| | | |
|---|---|---|
| 1,444,359 | 4/1971 | Germany |
| 6,512,957 | 4/1967 | Netherlands |

OTHER PUBLICATIONS

Sherwood & Pigford, "Absorption & Extraction", Chem. Engr. Series, 2nd. Ed., pp. 399–403, McGraw-Hill, 1952.

"Chem. Engr's Hndbk", Perry, 3rd Ed., 1950, McGraw-Hill, 1950, pp. 639–651.

"Chem Engr's Hndbk", Perry, 4th Ed., McGraw-Hill, pp. 14-40 to 14-43.

Primary Examiner—Frank W. Lutter
Assistant Examiner—Frank Sever

[57] ABSTRACT

In a process of extractive distillation, the combination of operating with two liquid phases in at least the uppermost trays of the column, preferably while maintaining the column operation at substantially an optimum reflux ratio, results in increased efficiencies and minimum requirements for selective solvent.

21 Claims, 5 Drawing Figures

EXTRACTIVE DISTILLATION

This is a continuation of Ser. No. 474,498 filed May 30, 1974, now abandoned.

FIELD OF THE INVENTION

The invention relates to a process of extractive distillation.

BACKGROUND OF THE INVENTION

Extractive distillation processes have been employed for the separation of various mixtures of components which cannot be feasibly separated by ordinary distillation, such as fractional distillation, particularly where the relative volatilities of individual components are very close or approximately equal.

SUMMARY OF THE INVENTION

In a process of extractive distillation, by operating with two liquid phases in at least the uppermost trays of the distillation column and by operating my column preferably at substantially optimum reflux ratio, I have found that I obtain the advantage of using a much reduced ratio or amount of highly selective solvent. Furthermore, I have found that my method increases the efficiency of separation by operating with two liquid phases. No one heretofore has recognized the advantages to be gained by operating with an extractive distillation process a highly selective solvent under two liquid phase conditions with suitable reflux ratios, and preferably substantially optimum reflux.

DETAILED DESCRIPTION OF THE INVENTION

As summarized above, I have discovered that by operating my extractive distillation process and column means with two liquid phases, in at least the uppermost trays of the column, and employing a highly selective solvent and suitable overhead reflux, that efficient separation is obtained effectively and economically, far outweighing any possible disadvantages of coexistence of two liquid phases under such conditions. The overhead reflux ratio can be as desired for efficient separation, so long as two liquid phases are maintained. Preferably, the reflux ratio will be close to optimum. While others have developed methods for avoiding two liquid phases, such as using a highly selective solvent and not applying reflux to the extractive distillation column such as in U.S. Pat. No. 3,338,824, I have discovered that the combination of two liquid phases with proper reflux ratio provides an effective separation method that increases overall operating efficiencies.

DETAILED DESCRIPTION OF THE INVENTION

Figure 1:
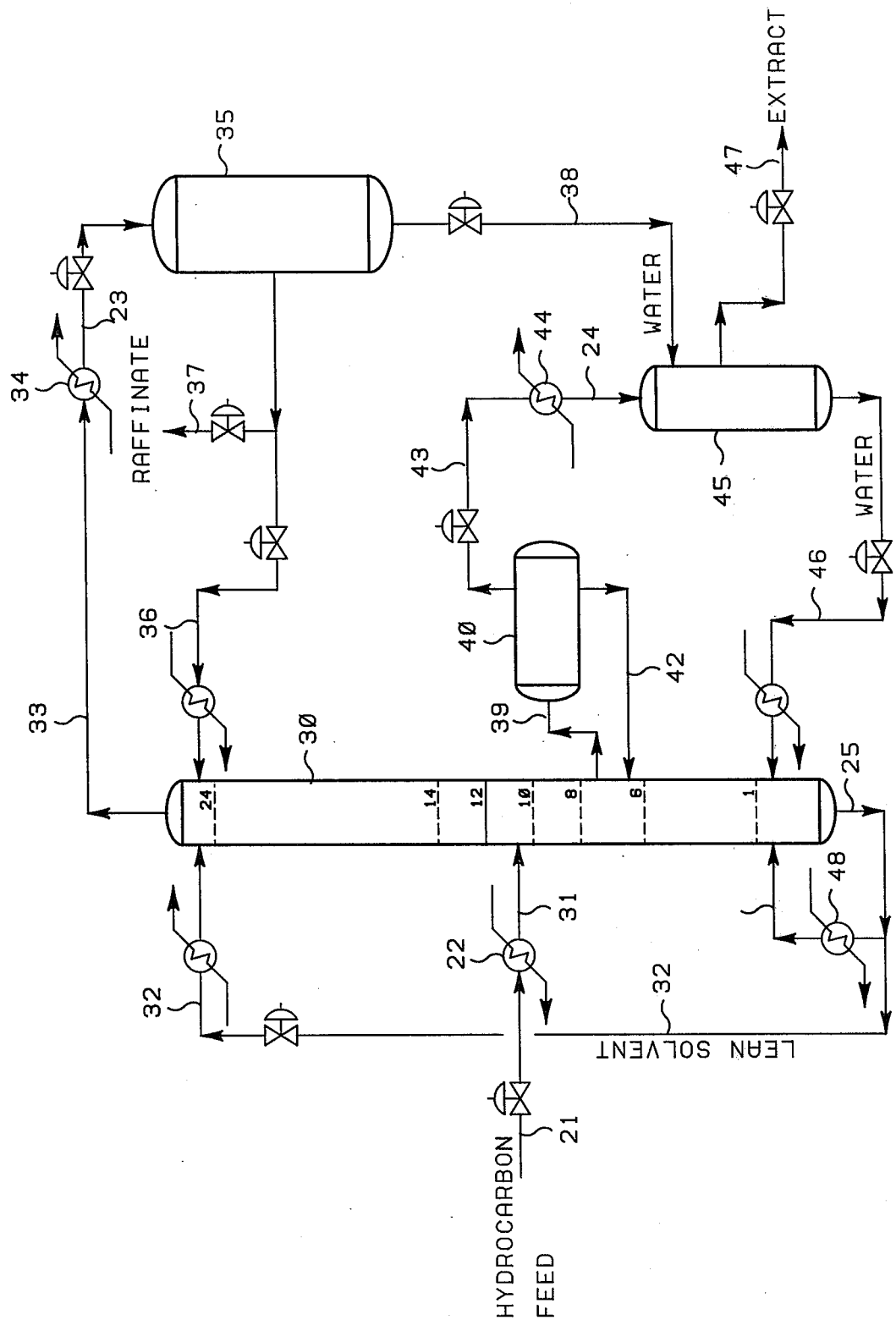
FIG. 1 illustrates the application of my two liquid phase process to the separation of components from a catalytically cracked gasoline described in Example I.

In a process of extractive distillation, a low-volatility agent is added to the mixture of organic components to be separated whereby the relative volatilities of the original components are changed to a sufficient extent as to result in sufficient difference in volatilities of the component such that separation by distillation becomes possible. Such a process is described for example in *Perry's Chemical Engineering Handbook*, 3rd Edition, McGraw Hill Company 1950, pages 634 through 651.

The low-volatility agent to be added usually is termed a "selective solvent", and usually is chosen for the maximum "selectivity" exhibited by the agent in the mixture of components to be separated. Selectivity is a term related to the change in volatilities of the feedstock components effected by the presence of the separating agent, with the higher the selectivity the greater the difference in volatilities resulting, and hence the easier the separation would become in terms of distillation trays. The lower the solubility of the feedstock components in the separating agent, the higher is the selectivity of the agent. However, where solubilities of the feedstock components are very low, and thus the selectivity very high, it has been necessary to operate the extractive distillation column with an extremely large amount of selective solvent in order to adequately dissolve one or more components from the feed mixture. Extremely large amounts of solvent are inefficient and undesirable economically.

Operation with two liquid phases has been suggested as a broad generalized teaching in such as U.S. Pat. No. 2,257,283 and U.S. Pat. No. 2,501,114. Operation with less solvent quantity of a very highly selective solvent results in operation with two immiscible liquid phases, one liquid phase in the column being solvent rich, the other liquid phase being relatively rich in feedstock components.

However, other than these generalized suggestions, all specific teachings in the prior art have been that an extractive distillation process and column should not be operated with two liquid phases. Refer *Perry's Handbook, supra* pages 644, specifically teaching that the selective solvent and extractive distillation operating conditions should be chosen so as to avoid the formation of immiscible liquid phases between the solvent and components in the extractive distillation column means. It is there discussed that if a solvent that is too selective is introduced, so that immiscibility occurs, the liquids in the column would be composed of a feedstock-rich phase and a solvent-rich phase, and that the concentration of the solvent in the feedstock-rich phase usually would be insufficient to enhance the volatility of the component to the desired extend so as to permit separation. Other art, such as U.S. Pat. No. 3,338,824, comments that if two liquid phases are formed when employing selective separating agents, that poor separating efficiency results.

The increased efficiencies, however, of my extractive distillation process now make it feasible to reduce operating costs in the separation of feedstocks which presently are being separated by less efficient distillation processes, and also to make new separations feasible which heretofore have been impossible to make via extractive distillation routes.

My novel process comprises the process of extractive distillation of an admixture of miscible organic components wherein at least two of said components exhibit relatively close volatilities, which comprises contacting said admixture with a highly selective solvent thereby increasing the difference in volatilities of said components, and thereafter extractively distilling said admixture in the presence of said selective solvent to form an overhead comprising the more volatile of said components, and a bottoms comprising the less volatile of said components and said selective solvent, separating said selective solvent from said bottoms, and recycling said separated solvent to said contacting step as said selective solvent, refluxing at least a portion of said overhead at reflux ratios sufficient to maintain two immiscible liquid phases.

My process further can be described as a process for separating a feedstock stream containing two or more components of essentially identical volatilities which comprises the steps of contacting said feestock under extractive distillation conditions with lean selective solvent effective to substantially change the volatilities of said components, forming an overhead stream of the more volatile components, and a bottoms comprising solvent and less volatile components, withdrawing overhead vapors from said extractive distillation means comprising the more volatile of said components, condensing and returning as reflux to said extractive distillation means at least a portion of said overhead in amounts sufficient to form in at least a portion of the distillative means of said extractive distillative means two immiscible liquid phases comprising a solvent rich phase and a phase rich in said more volatile component, separating said bottoms stream into streams comprising said lean selective solvent and said less volatile components, recycling said lean selective solvent to said contacting step and recycling at least a portion of said lesser volatile components to said extractive distillative means as stripping vapor therein.

My process also comprises a method to increase substantially the efficiency of an extractive distillation process for extracting at least one organic component from an admixture of organic components wherein the volatilities of at least two said components are sufficiently close as to preclude effective separation by fractional distillation, wherein the improvement comprises the step of adding to said admixture a selective solvent effective to create a significant difference in volatilities of said components so as to permit separation of said components by extractive distillation, and wherein said extractive distillation process is conducted under conditions and ratios of solvent to feedstock and ratios of overhead reflux effective to maintain two liquid immiscible phases comprising a solvent-rich phase and said reflux in said extractive distillation.

EXAMPLES OF SYSTEMS USING MY INVENTION

Examples of system wherein the operating costs for separation of feedstocks can be reduced include such as the separation of butadiene from butenes and butanes; separation of isoprene from amylenes and pentanes; separation of benzene, toluene, xylenes, BTX, from a reformate feedstock which also contains naphthenes and paraffinics; and separation of naphthenes such as cyclohexane from closely boiling paraffins such as the hexanes.

Reduced operating costs can be obtained in such separations since less solvent is being circulated and fewer trays are needed, or both, from the requirements of previous processes where two liquid phases specifically were avoided by using increased amounts of highly selective solvent, or by using lower amount of a less selective solvent, or by avoiding reflux in the column.

Exemplary of new separations which can be made in accordance with the process of my invention include the separation of $C_6$ through $C_9$ aromatics from a pyrolysis gasoline stream obtained by catalytic or thermal cracking of gas oil or similar feedstocks. Such a feedstream contains $C_6$ through $C_9$ olefins, and previously it has been found not feasible to separate out the aromatics in sufficiently high purity from the olefins so as to be worthwhile. Consequently, the presently employed procedures have been wasteful of the olefinics, since procedure has been to selectively hydrogenate such a feedstock, converting the olefinics to paraffinics, which latter were easily separated from the aromatics.

I have incorporated my novel process of extractive distillation into a scheme for separation of pyrolysis gasoline into various respective components. More particularly, pyrolysis gasoline was fractionally distilled and the center fraction containing $C_7$ through $C_{10}$ hydrocarbons is separated by extractive distillation into a raffinate containing paraffins, naphthenes, and olefins of $C_7$ through $C_{10}$, and an extract of aromatics and $nC_p+$ paraffins. The latter stream is fractionated to recover benzene, toluene, xylenes, and a stream containing $C_9+$ aromatics plus $nC_9+$ paraffins. The latter stream is extractively distilled so as to separate the $nC_9+$ paraffins from the $C_9+$ aromatics. If desired, this second extractive distillation can be carried out on the stream between the toluene fractionator and the xylenes fractionator. This scheme is further illustrated by examples contained in my specification.

In accordance with my discovery, my invention can be applied to separate a stream of high purity aromatics ranging from toluene through $C_{10}$ aromatics from a cut of cracked gasoline containing such aromatics without the necessity for preliminary hydrogenation step to eleminate the olefins associated with the aromatics.

Another application feasible according to the process of my invention involves treatment of a catalytically cracked gasoline fraction by my two liquid phase extractive distillation process so as to remove the bulk of sulfur-containing compounds. As is known, gasoline utilized for automotive purposes contains sulfur compounds, under present requirements use oxidation catalysts in automotive emissions control, results in the formation of various sulfur oxides such as $SO_3$, and with moisture $H_2SO_4$, which are injurious. The sulfur content of motor fuels must be reduced to very low levels, and even lower under future regulations, such as 30 to 1000 ppms, and expectedly lower. Most sulfur in present motor fuel comes from catalytically cracked gasoline fractions. the conventional present approach is by hydrotreating so as to remove sulfur-containing compounds to a workable level. Unfortunately, simultaneously the result is hydrogenation of olefinics to a low octane paraffinic content, reducing the overall octane number of the gasoline fraction, and necessitating reforming to raise the octane level up to satisfactory levels. Many of the olefinics present have in the process become $C_5$ to $C_7$ paraffins which cannot be satisfactorily reformed. Instead of this conventional approach, my invention can be employed to apply a two-liquid phase extractive distillation so as to remove the bulk of the sulfure compounds with the aromatics, and then selectively hydrotreating such stream. This leaves the olefins in the saturated, raffinate stream, reducing the size consequently of any necessary hydrotreating for the olefins, and reduces extensively the hydrogen requirements otherwise necessary.

Applications of may invention can be further understood in accordance with following examples which are included to assist in an understanding of the scope of my invention, in an understanding of various applications, without necessarily limiting my invention to specific examples.

Solvents capable of selectively dissolving and extracting aromatic hydrocarbons from a mixture of aromatic and nonaromatic hydrocarbons are known. Preferred type of selective solvent is the compounds generally known as the "sulfolane-type". The sulfolane type solvent posses a 5 membered ring containing one atom of sulfur and 4 atoms of carbon with 2 oxygen atoms bonded to the sulfur atom of the ring. Generically, the sulfolane type solvents have a structural formula as noted by Formula 1:

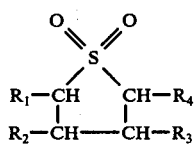

(1)

wherein $R_1$, $R_2$, $R_3$, and $R_4$ are independently selected from the group comprising a hydrogen atom and alkyl group having from 1 to 10 carbon atoms, an alkoxy radical having from 1 to 8 carbon atoms, and an arylalkyl radical having from 1 to 12 carbon atoms.

Other solvents analogous to the sulfolane type solvents which may be included with this process are sulfolenes such as 2-sulfolene or 3-sulfolenes which have the structure as illustrated in formulas 2 and 3:

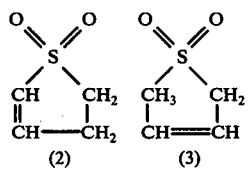

(2)    (3)

Other typical solvents which have a high selectivity for separating aromatics from non-aromatic hydrocarbons and which may be processed within the scope of the present invention are 2-methylsulfolane, 2,4-dimethylsulfolane, methyl 2-sulfonyl ether, n-aryl-3-sulfonyl amine, 2-sulfonyl acetate, diethylene glycol, various polypropylene glycols, dimethyl sulfoxide, N-methyl pyrollidone, etc.

A specifically preferred solvent chemical to be utilized in accordance to formula 1, $R_1$, $R_2$, $R_3$ and $R_4$ each comprise a hydrogen atom. The structural formula of solfolane is set out in Formula 4:

(4)

-continued

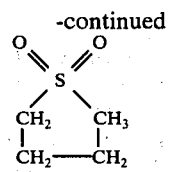

Since these aromatic selective solvents are well known to those trained in the art and, in particular, since sulfolane type solvents are articles of commerce widely utilized in the solvent extraction art, greater detail thereon need not be pesented herein.

The aromatic selectivity of aromatic selective solvents such as sulfolane can usually be enhanced by the addition of water to the solvent. Preferably the solvent utilized in the practice of this invention contains small quantities of water to increase the selectivity of the overall solvent phase for the aromatic hydrocarbons without reducing in a substantial manner, the solubility of the solvent in the aromatics. Further, the presence of water in the solvent composition provides a relatively volatile material which can be distilled from the solvent to vaporize the last traces of non-aromatic hydrocarbons from the solvent stream by steam distillation. Accordingly, a preferred solvent composition to be utilized in the process of the present invention contains about 0.1% to about 20% by weight water and more particularly from about 0.5 to about 1% by weight, depending upon the particular solvent utilized and the process conditions at which the solvent extraction zone and extractive distillation zone are operated.

In addition to or without water, the sulfolane solvent may be used in admixture with other solvents such as diethylene glycol and the other numerous glycols, the various glycol ethers such as ethylene glycol monomethyl ether and diethylene glycol monomethyl ether, the various alcohols such as metanol, the various ketones such as acetone, and the like.

EXAMPLE I

To demonstrate the increased separation efficiency of two-liquid-phase extractive distillation, a full range catalytically cracked gasoline was fractionated to obtain a center-cut fraction including the $C_7$ through $C_{10}$ hydrocarbons. Analyses of the gasoline feedstock and of the center-cut fraction were as follows:

TABLE I

Analysis of Catalytically Cracked Gasoline Fractions

| | Feedstock | Light Fraction | Heavy Fraction | Center-cut Fraction |
|---|---|---|---|---|
| Percent of of Feedstock Composition, Vol. % | 100 | 36 | 18 | 46 |
| Paraffins | 35.9 | | 20.5 | 20.0 |
| Naphthenes | | 99.4 | 14.3 | 18.0 |
| Olefins | 38.1 | | 9.1 | 30.1 |
| Aromatics | 26.0 | 0.6 | 56.1 | 37.9 |

The aromatic content of the center-cut fraction was analyzed to be almost entirely $C_7$ through $C_{10}$ aromatics.

The center-cut fraction was separated into an aromatic-rich extract (kettle) product and an aromatic-lean raffinate (overhead) product by two-liquid phase extractive distillation as illustrated in

FIG. 1

Distillation column 30 was 18 inches in diameter and contained 24 valve-type contacting trays. Hydrocarbon feedstock 21 was passed through a heat exchanger 22 to the column 30 on the 10th tray via line 31. Lean solvent 32 was passed to the top of column 30. Overhead vapors 33 were removed, condensed in water-cooled heat exchanger 34, and the condensate 23 passed to reflux accumulator 35. Part of the overhead condensate was returned 36 to the top of column 30 as reflux, and most of the remainder removed as raffinate product 37. A small amount of water separates in the bottom of accumulator 35 and can be withdrawn 38, the water having entered the system as part of the solvent as explained later hereinafter. The upper 18 trays of column 30, that is, trays No. 7 through No. 24, operate as extractive distillation means. The lower 6 trays acted as solvent stripper means, that is, the extract product was stripped from the rich solvent. The extract product 39 was removed from column 30 in the vapor state and passed to liquid knockout vessel 40 wherein any entrained liquid was settled out with assistance of a demister element (not shown). The recovered liquid 42 was returned to column 30. Extract vapors 43 were passed through condenser 44 and the liquid condensate 24 therefrom passed into accumulator-separator tank 45. Entrained water in condensate 24 together with water from accumulator 35 settle in the bottom of separator 45 and can be removed 46 for return to the bottom of column 30. Liquid extract product was recovered 47 from separator 45.

Column 30 was reboiled by recycling some of the bottoms 25 therefrom through heater 48 wherein it is vaporized and the vapor returned 49 to column 30. Remaining bottoms is recycled 32 as lean solvent to the top of column 30. Water 46 introduced into the bottom of column 30 is largely returned 32 to the top of the column 30 with the solvent. Incoporating a small amount of water into the solvent is sometimes desirable as a means of adjusting solvent selectivity and solubility and therefore separation efficiency as explained hereinafter.

Column 30 was operated at 15 psig pressure in separating the feedstock of Table I using sulfolane as selective solvent further containing about 2.3 wt. % water. Column operating conditions are given in Table II below:

TABLE II

OPERATING DATA FOR EXTRACTIVE DISTILLATION OF $C_7$–$C_{10}$ CUT OF CAT-CRACKED GASOLINE

| Run No. | 1 | 2 | 3 |
|---|---|---|---|
| Flow Rates, lb/hr - | | | |
| Solvent (32) | 5820 | 3530 | 2850 |
| Hydrocarbon Feed (21) | 1550 | 972 | 777 |
| Extract Product (47) | 500 | 523 | 501 |
| Raffinate Product (37) | 1050 | 471 | 302 |
| Stripping Steam to Kettle (46) | 785 | 625 | 625 |
| Water with Extract (43) | 590 | 560 | 575 |
| Water with Raffinate (38) | 195 | 65 | 50 |
| Hydrocarbon Reflux (36) | 844 | 490 | 339 |
| Reflux Ratio, reflux/raffinate | 0.80 | 1.04 | 1.12 |
| Moles Stripping Steam/Mole Solvent | 0.90 | 1.18 | 1.46 |
| Yield of Feed as Extract, % | 33.3 | 52.7 | 62.4 |
| Solvent/Hydrocarbon Feed Ratio | 3.76 | 3.64 | 3.67 |
| Aromatics Concentration, wt. % - | | | |
| Feed | 37.9 | 37.9 | 37.9 |
| Extract | 87.4 | 77.1 | 70.5 |
| Raffinate | 13.0 | 3.1 | 1.8 |
| Aromatics Recovery in Extract, % | 76.2 | 96.5 | 98.7 |
| Temperatures, ° F - | | | |
| Hydrocarbon Feed | 307 | 329 | 350 |
| Solvent Feed | 273 | 267 | 245 |
| Reflux | 273 | 267 | 262 |
| Stripping Steam to Kettle | 265 | 314 | 319 |
| Kettle | 366 | 362 | 356 |
| Tray 1 | 295 | 305 | 312 |
| Tray 6 | 295 | 298 | 309 |
| Tray 12 | 290 | 284 | 285 |
| Tray 18 | 287 | 278 | 275 |
| Tray 24 | 272 | 266 | 260 |
| Column Differential Press., in. $H_2O$ | 51 | 50 | 46 |
| Water in Lean Solvent, wt. % | 2.3 | 2.3 | 2.2 |

Analyses of the feedstock, raffinate, and extract products for the three runs of Table II are given in Table III below as follows:

TABLE III

| | | 1 | | 2 | | 3 | |
|---|---|---|---|---|---|---|---|
| Run No. | Feed | Raff. | Extr. | Raff. | Extr. | Raff. | Extr. |
| PONA Analysis, Volume % | | | | | | | |
| Paraffins | 20.6 | 28.9 | 3.0 | 32.3 | 6.0 | 34.5 | 7.7 |
| Olefins | 30.7 | 40.8 | 6.7 | 44.7 | 11.7 | 44.1 | 15.0 |
| Naphthenes | 13.3 | 18.0 | 3.2 | 19.1 | 5.7 | 19.6 | 7.9 |
| Aromatics | 35.4 | 12.3 | 88.2 | 3.9 | 76.6 | 2.0 | 69.4 |
| [a]Nitrogen, ppm | 21 | 13 | — | 6 | — | 4 | 18 |
| [a]Sulfur, ppm | 646 | 150 | 1300 | 51 | 1200 | 43 | 888 |
| RON[b]Clear | 89.7 | 81.0 | 103.9 | 79.6 | 100.3 | 78.3 | 98.1 |
| MON[c]Clear | 79.2 | 73.5 | 91.9 | 72.8 | 88.0 | 72.4 | 85.5 |

[a]After six stages of water wash
[b]Research Octane Number
[c]Motor Octane Number Referring to the results of Table III, it is observed from Run No. 1 that the olefin content of the feedstock was reduced from 30.7 volume percent to 6.7 volume percent in the extract product while the aromatic content was increased from 35.4 volume percent to 88.2 volume percent. This is a remarkable separation when it is considered that only 4 extractive distillation trays were used below the point of feed entry, trays 6 through 10, in separating the aromatics from the olefins.

Heretofore it had been considered impossible to separate olefins from aromatics in such a wide-boiling feedstock as a $C_7$ through $C_{10}$ fraction because the highest boiling $C_{10}$ olefins tend to exhibit about the same volatility as the lowest boiling of the aromatics, toluene, under conventional extractive distillation operation. It had previously been necessary to try to avoid this problem of separating the high-boiling olefins from the low-boiling aromatics by hydrogenating the feedstock and thus converting the olefins to paraffins, with consequent economic loss of the potentially valuable olefins.

Figure 2:
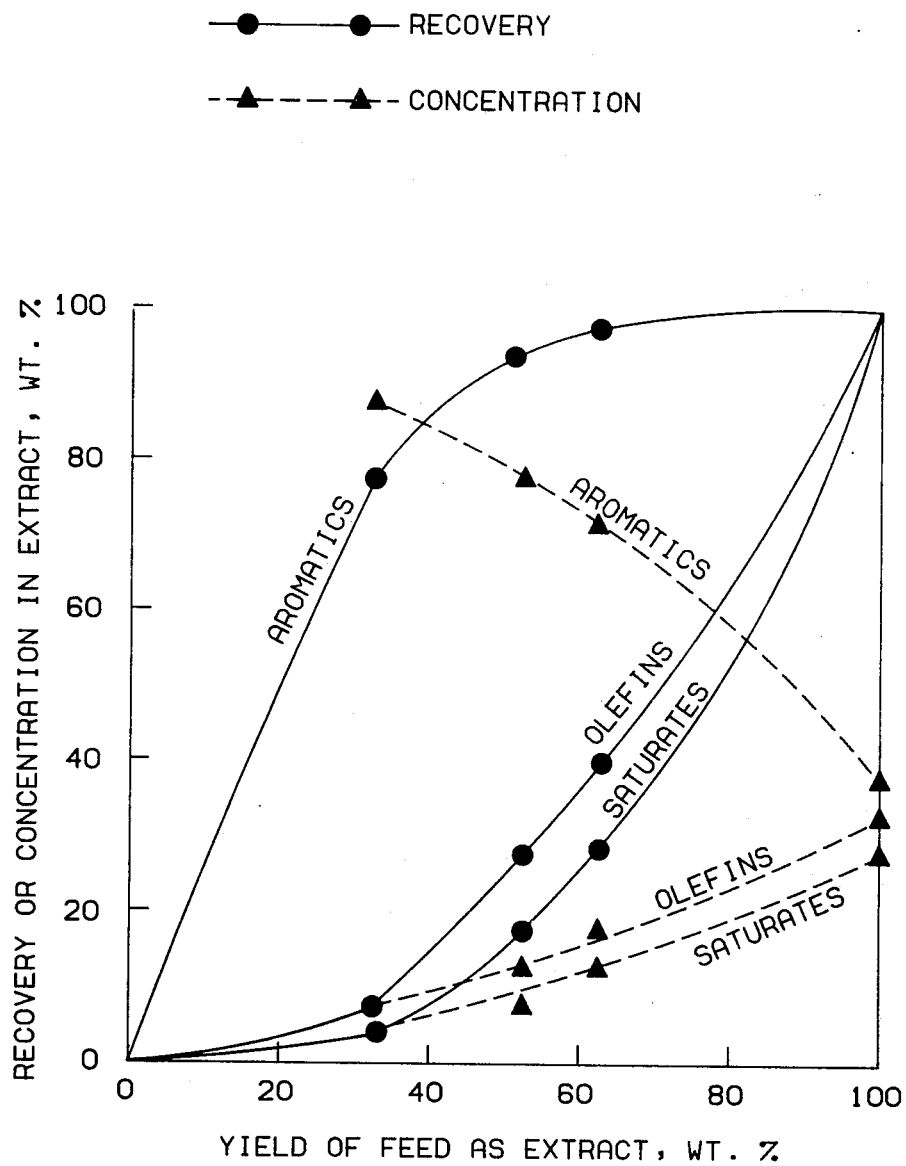
FIG. 2 graphically illustrates data obtained in Example I in the separation of paraffins, olefins, naphthenes, and aromatics, with the paraffins and naphthenes included together as saturates.

The ability of sulfolane to effectuate separation between olefins and paraffins is further dramatically illustrated in FIG. 2 wherein the data from Tables II and III are plotted, showing recovery or concentration in the extract of a given component is weight percent against yield of feed as extract in weight percent. Paraffins and naphthenes are summed together as Saturates in FIG. 2. The spread between Aromatics and Olefins is almost as great as between Aromatics and Saturates.

By use of the increased separation efficiency of the two-liquid-phase extractive distillation process, it thus has become feasible to separate olefins from aromatics where both are contained in a wide boiling range stream.

Referring to FIG. 1 and to the operating conditions employed in Run A as tabulated in Table II, it can be observed that the rate of flow of solvent, sulfonane plus water 32 to to the top of column 30 was 5820 pounds per hour. The rate of reflux 36 flow to the top of column 30 was 844 pounds per hour.

According to the prior art, it would be necessary to employ sufficient solvent passed to the top of an extractive distillation column so as to effectively dissolve all the reflux. But in my process, it is clear that 5820 pounds of sulfolane containing 2.3 weight percent water cannot completely dissolve 844 pounds of reflux hydrocarbon of the composition given in Table III for the raffinate for Run No. 1. Consequently two liquid phases, one solvent-rich and the other hydrocarbon-rich, have descended in column 30. Any possible undesirable effects to separation efficiency caused by the presence of the second liquid phase, as prior art teaches, was more than outweight by the increased separation efficiency obtained by use of a highly selective solvent, also as taught by prior art. The increase in efficiency obtained by use of a highly selective solvent has been demonstrated to more than overcome any possible decrease in efficiency produced by the presence of a second liquid phase.

EXAMPLE II

In another demonstration of the separation efficiency of two-liquid-phase extractive distillation, a reformate fraction containing $C_6$ through $C_8$ aromatics, benzene through xylenes together with paraffins and naphthenes having the same boiling range, was separated in the same column as used and described for Example I. Composition of this feedstock was are follows:

| Feedstock Component | Wt. % |
|---|---|
| Propane + Butanes | 0.05 |
| Pentanes | 0.15 |
| n-Hexane | 5.1 |
| Other hexanes | 6.2 |
| Heptanes | 30.0 |
| Octanes | 27.8 |
| Nonanes + Decanes | 0.87 |
| Benzene | 3.8 |
| Toluene | 23.4 |
| Ethyl Benzene | 1.00 |
| p-xylene | 0.45 |
| m-xylene | 1.02 |
| o-xylene | 0.11 |
| $C_9$ + aromatics | trace |

The above feedstock was separated in the same column as described in Example I using sulfolane plus about 2 wt. % water as selective solvent, employing a constant solvent-to-feedstock ratio of 2.43 pound per pound, a column pressure of 15 psig, and employing various reflux ratios as tabulated in the following Table IV of operating results. A constant solvent rate of 5450 lb/hr was used while the reflux rate was varied from 590 lb/hr to 1180 lb/hr to determine the optimum reflux ratio. Under all conditions, however, the solvent rate was insufficient to dissolve all of the reflux and therefore two-liquid phases descended in the column.

TABLE IV

| | Operating Data for Aromatics Extraction from $C_6$-$C_8$ Reformate Cut | | | | | | | | |
|---|---|---|---|---|---|---|---|---|---|
| Run No. | 1 | 2 | 3 | 4 | 5 | 6 | 7 | 8 | 9 |
| Flow Rates, lb/hr - | | | | | | | | | |
| Solvent (32) | 5450 | 5450 | 5450 | 5450 | 5450 | 5450 | 5450 | 5450 | 5450 |
| Hydrocarbon Feed (31) | 2240 | 2240 | 2240 | 2240 | 2240 | 2240 | 2240 | 2240 | 2240 |
| Extract (47) | 765 | 765 | 765 | 765 | 765 | 765 | 765 | 765 | 765 |
| Raffinate (37) | 1475 | 1475 | 1475 | 1475 | 1475 | 1475 | 1475 | 1475 | 1475 |
| Stripping Steam to | | | | | | | | | |
| Kettle (46) | 500 | 500 | 525 | 500 | 500 | 510 | 510 | 510 | 510 |
| Water with Extract (43) | 405 | 405 | 415 | 415 | 405 | 405 | 405 | 415 | 425 |
| Water with Raffinate (38) | 95 | 95 | 110 | 85 | 95 | 105 | 105 | 95 | 85 |
| Reflux (36) | 590 | 885 | 1180 | 590 | 885 | 1180 | 1180 | 885 | 590 |
| Reflux Ratio, lb. | | | | | | | | | |
| reflux/lb. raffinate | 0.40 | 0.60 | 0.80 | 0.40 | 0.60 | 0.80 | 0.80 | 0.60 | 0.40 |
| Feed Vaporized, % | 55 | 55 | 55 | 66 | 67 | 67 | 82 | 84 | 84 |
| Yield of Feed as Extract, wt.% | 34.1 | 34.1 | 34.1 | 34.1 | 34.1 | 34.1 | 34.1 | 34.1 | 34.1 |
| Aromatics Concentration, wt.% | | | | | | | | | |
| Feed | 34.2 | 34.6 | 34.6 | 34.6 | 35.1 | 34.8 | 33.9 | 34.8 | 34.5 |
| Extract | 91.5 | 93.2 | 91.8 | 91.6 | 92.5 | 90.9 | 91.9 | 93.3 | 91.8 |
| Raffinate | 5.8 | 5.1 | 5.6 | 5.2 | 4.9 | 5.4 | 5.5 | 5.0 | 5.6 |
| Recovery of Aromatics | | | | | | | | | |
| in Extract, wt. % | 89.3 | 90.4 | 89.6 | 90.1 | 90.7 | 89.7 | 89.7 | 90.7 | 89.4 |
| Temperatures, ° F | | | | | | | | | |
| Hydrocarbon Feed | 258 | 258 | 259 | 264 | 263 | 264 | 267 | 268 | 267 |
| Solvent Feed | 238 | 238 | 239 | 237 | 240 | 238 | 238 | 239 | 238 |
| Reflux | 238 | 238 | 238 | 238 | 239 | 238 | 238 | 240 | 240 |
| Stripping Steam to Kettle | 336 | 335 | 334 | 333 | 333 | 334 | 334 | 334 | 334 |

TABLE IV-continued

| | Operating Data for Aromatics Extraction from $C_6$-$C_8$ Reformate Cut | | | | | | | | |
|---|---|---|---|---|---|---|---|---|---|
| Run No. | 1 | 2 | 3 | 4 | 5 | 6 | 7 | 8 | 9 |
| Kettle | 362 | 365 | 361 | 364 | 363 | 363 | 365 | 363 | 363 |
| Tray 1 | 294 | 292 | 288 | 298 | 295 | 293 | 296 | 300 | 303 |
| Tray 6 | 280 | 276 | 271 | 282 | 280 | 277 | 284 | 287 | 288 |
| Tray 12 | 250 | 246 | 246 | 251 | 248 | 250 | 250 | 250 | 253 |
| Tray 18 | 247 | 242 | 242 | 247 | 242 | 242 | 243 | 243 | 247 |
| Tray 24 | 236 | 236 | 236 | 237 | 237 | 234 | 236 | 238 | 237 |
| Column Differential Pressure, in $H_2O$ | 48 | 50 | 52 | 50 | 50 | 52 | 52 | 50 | 49 |
| Water in Lean Solvent, wt.% | 2.2 | 2.1 | 2.1 | 2.3 | — | 2.3 | 2.2 | 2.5 | 2.9 |

Figure 3:
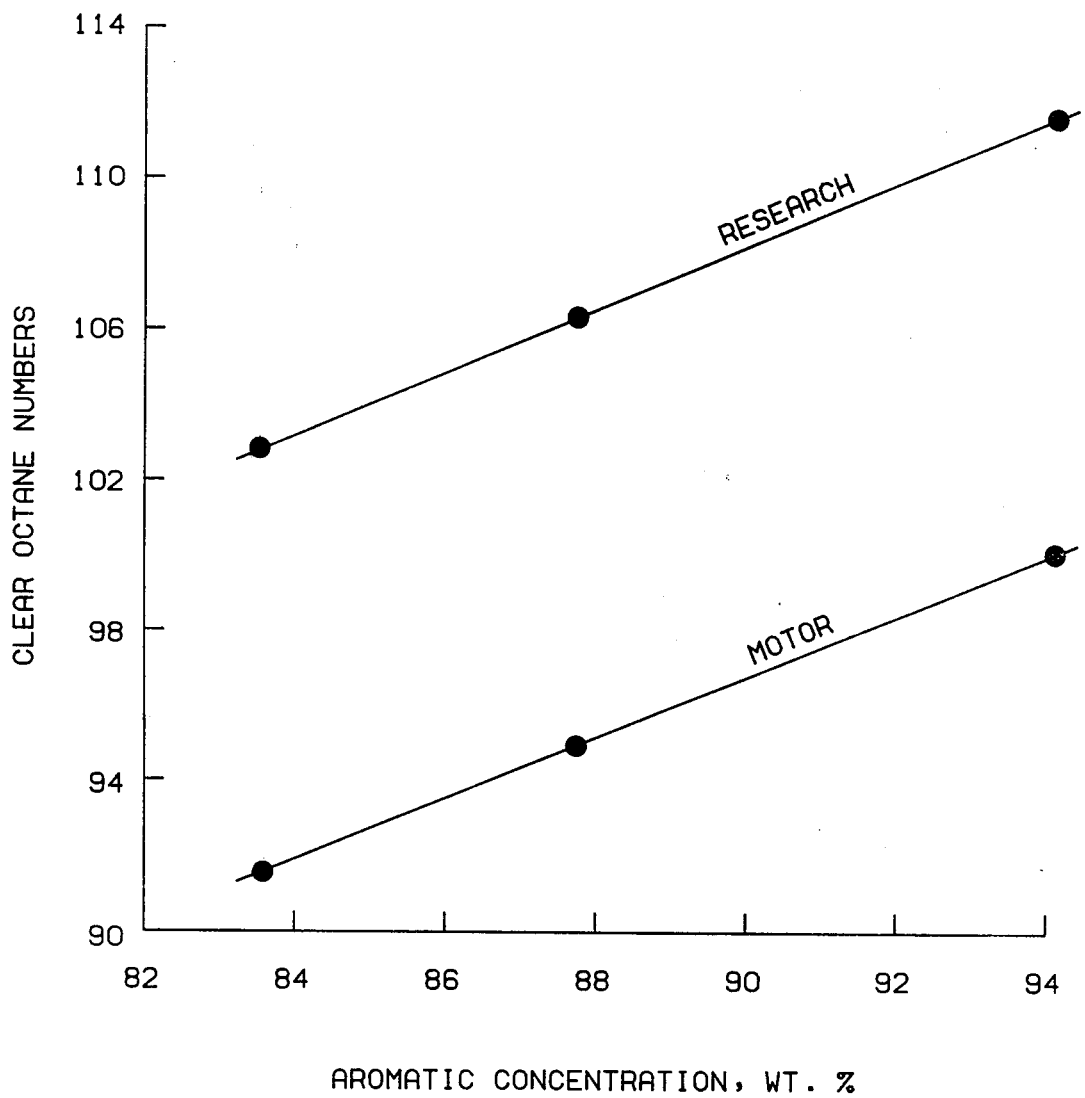
FIG. 3 graphically portrays the increased RON and MON resulting from the high aromatic concentration achievable in my separation process applied to a $C_6$-$C_8$ reformate art.

Research and motor octane results are plotted in FIG. 3, showing the clear octane values obtained plotted against aromatic concentration wt. % taken from above results.

Inspection of the results shows that an extract product was obtained with an aromatic content of from 90.9 to 93.3 wt. % from a feedstock containing only about 35 wt. % aromatics using only 4 fractionation trays between the point of feedstock entry into the column and the point of extract product withdrawal which were the same as described in Example I and as illustrated in FIG. 1.

Figure 4:
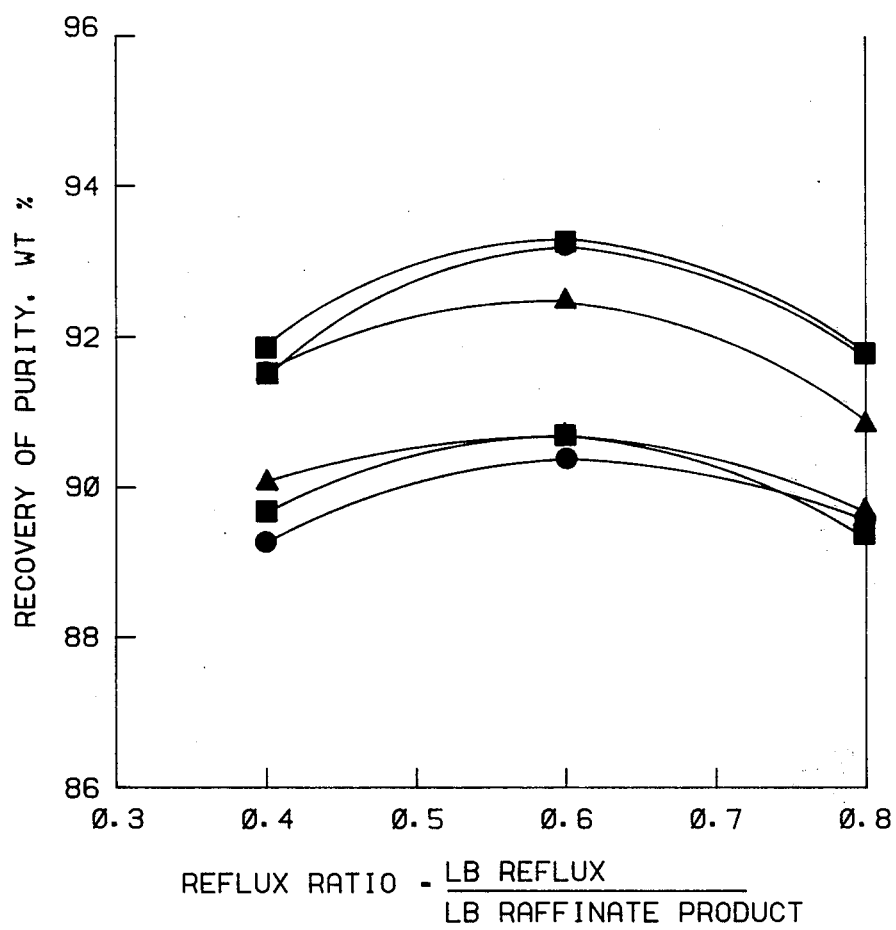
FIG. 4 plots data from Example II to demonstrate aspects of optimum reflux ratio.

That an optimum reflux ratio exists for an extractive distillation operation, is illustrated by plotting the data from Table IV as FIG. 4. The data illustrate in this fashion that maximum purity and recovery of aromatics in the extract product was obtained with a reflux ratio of about 0.5–0.7, preferably 0.6. At higher and lower reflux ratios, both purity and recovery decreased. Two liquid phases descended in the column at all the reflux ratios tested and plotted. Only by decreasing the reflux ratio to some value much below 0.4 would the column operate with one liquid phase (solvent) but at a much lower recovery and purity of the aromatic product.

EXAMPLE III

To demonstrate the increased aromatic product purity obtainable by using more fractionation trays, the same feedstock as described in Example II was passed to tray No. 14 in the column, rather than to tray No. 10 as in the runs of Example II, and a series of tests were made with 8 trays between point of feedstock entry and extract product withdrawal as contrasted to only 4 trays for the runs of Example II. The results so obtained are summarized in Table V below:

TABLE V

| | Operating Data for High Purity Aromatics Extraction from $C_6$-$C_8$ Reformate Cut | | | | | |
|---|---|---|---|---|---|---|
| Run No. | 10 | 11 | 12 | 13 | 14 | 15 |
| Flow Rates, lb/hr | | | | | | |
| Solvent (32) | 6550 | 6550 | 6550 | 6550 | 6550 | 6550 |
| Hydrocarbon Feed (31) | 2240 | 2240 | 2230 | 2230 | 2230 | 2230 |
| Extract (47) | 765 | 710 | 660 | 650 | 650 | 650 |
| Raffinate (37) | 1475 | 1530 | 1570 | 1580 | 1580 | 1580 |
| Stripping Steam to Kettle (46) | 500 | 500 | 500 | 500 | 500 | 500 |
| Water with Extract (43) | 405 | 405 | 395 | 405 | 390 | 365 |
| Water with Raffinate (45) | 95 | 95 | 105 | 95 | 110 | 135 |
| Reflux (36) | 885 | 885 | 880 | 590 | 1180 | 1580 |
| Reflux Ratio, lb. reflux/lb. raffinate | 0.60 | 0.58 | 0.56 | 9.37 | 0.75 | 1.0 |
| Feed Vaporized, wt. % | 70 | 70 | 70 | 70 | 70 | 70 |
| Yield of Feed as Extract, wt. % | 34.1 | 31.7 | 29.6 | 29.1 | 29.1 | 29.1 |
| Aromatics Concentration, wt. % | | | | | | |
| Feed | 34.0 | 33.8 | 32.9 | 32.9 | 32.7 | 33.3 |
| Extract | 92.0 | 96.8 | 99.0 | 98.6 | 99.0 | 97.4 |
| Raffinate | 4.4 | 4.9 | 6.3 | 6.2 | 6.3 | 7.0 |
| Recovery of Aromatics in Extract, wt. % | 91.8 | 90.2 | 86.7 | 86.8 | 86.8 | 85.2 |
| Temperature, ° F | | | | | | |
| Hydrocarbon Feed | 261 | 263 | 263 | 262 | 263 | 261 |
| Solvent Feed | 239 | 238 | 238 | 238 | 238 | 238 |
| Reflux | 239 | 239 | 238 | 239 | 238 | 240 |
| Stripping Steam to Kettle | 334 | 334 | 333 | 333 | 334 | 330 |
| Kettle | 364 | 363 | 362 | 363 | 363 | 361 |
| Tray 24 | 236 | 236 | 237 | 236 | 236 | 234 |
| Column Differential Pressure, in $H_2O$ | 54 | 55 | 54 | 56 | 58 | 63 |
| Water in Lean Solvent, wt. % | 2.5 | 2.2 | 2.3 | 2.0 | 2.3 | 2.2 |
| Composition of Extract, wt. % | | | | | | |
| $C_6$ Paraffins | 0.02 | — | — | — | 0.05 | — |
| $C_7$ Paraffins | 0.60 | 0.20 | 0.07 | 0.14 | 0.05 | 0.08 |
| $C_8$ Isoparaffins | 5.3 | 2.3 | 0.75 | 1.1 | 0.79 | 1.9 |
| Normal Octane | 2.0 | 0.72 | 0.14 | 0.22 | 0.11 | 0.65 |
| Benzene | 7.7 | 7.4 | 6.0 | 7.1 | 5.5 | 4.0 |
| Toluene | 71.2 | 74.7 | 77.5 | 76.1 | 78.0 | 77.9 |
| Ethyl Benzene | 3.4 | 3.7 | 3.9 | 3.9 | 4.0 | 4.0 |
| p-xylene | 1.9 | 2.1 | 2.2 | 2.3 | 2.3 | 2.4 |
| m-xylene | 4.5 | 5.0 | 5.3 | 5.2 | 5.4 | 5.3 |
| o-xylene | 1.1 | 1.2 | 1.3 | 1.2 | 1.3 | 1.3 |
| $C_9$ + $C_{10}$ Benzenes | 2.2 | 2.7 | 2.8 | 2.8 | 2.5 | 2.5 |

The data in Table V demonstrate that an extract product containing as high as 99.0 wt. % aromatics in Run 14 is obtainable from a feedstock containing only 32.7 wt.% aromatics using only 8 fractionation trays between the point of feed entry and extract produce withdrawal by operating with a highly selective solvent, sulfolane plus water, under optimum reflux conditions and with two-liquid phases present in the top of the fractionator. Note also that the optimum reflux ratio has varied with adjusted point of feed of feedstock, broadly such as 0.3–1.1.

EXAMPLE IV

In additional demonstrations to illustrate the efficiency of 2-liquid-phase extractive distillation for the separation of diolefins, a separation that is more difficult than the separation of aromatics from olefins and paraffins, mixtures of butadiene and butene-1 were separated using mixtures of sulfolane and methyl carbitol as selective solvent. The extractive distillation column was 4 inches in diameter, contained 37 sieve-type trays with 29.7 percent open area, and was otherwise similar to the larger column shown in FIG. 1. The efficiency of the extractive distillation column in this series of tests was expressed in terms of "Separation Factor" calculated from the overhead (OH) and kettle (KP) compositions as follows:

$$\text{Separation Factor} = \frac{\text{Butene-1 in OH}}{\text{Butadiene in OH}} \times \frac{\text{Butadiene in KP}}{\text{Butene-1 in KP}}$$

To illustrate, in one test the overhead composition ws 70.7 wt. % butene-1 and 29.3 wt. % butadiene while the kettle product composition was 19.1 wt. % butene-1 and 80.9 wt. % butadiene.

Separation factor for the column efficiency is calculated as follows:

$$\text{Separation Factor} = \frac{70.7}{29.3} \times \frac{80.9}{19.1} = 10.2$$

The separation factor increases, of course, as the degree of separation increases in the column and would reach infinity upon obtaining pure butene-1 overhead and pure butadiene as bottoms product.

Data obtained in the first series of tests are tabulated below in Table VI.

TABLE VI

Separation of Butadiene and Butene-1
Solvent: 48 wt. % Sulfolane,
48 wt. % Methyl Carbitol
4 wt. % Water

| Run No. | Feed Composition, wt. % Butadiene | Solvent to Feed Ratio, lb/lb | Reflux Ratio, lb. Reflux per lb. OH Product | Separation Factor, SF |
|---|---|---|---|---|
| 1 | 60.6 | 7.0 | 1.00 | 7.97 |
| 2 | 60.9 | 7.0 | 0.57 | 7.69 |
| 3 | 53.9 | 7.0 | 1.57 | 5.61 |
| 4 | 54.3 | 7.0 | 2.21 | 6.99 |
| 5 | 54.1 | 7.0 | 2.60 | 7.85 |
| 6 | 53.8 | 7.0 | 3.14 | 10.09 |
| 7 | 53.4 | 7.0 | 3.79 | 7.00 |

Figure 5:
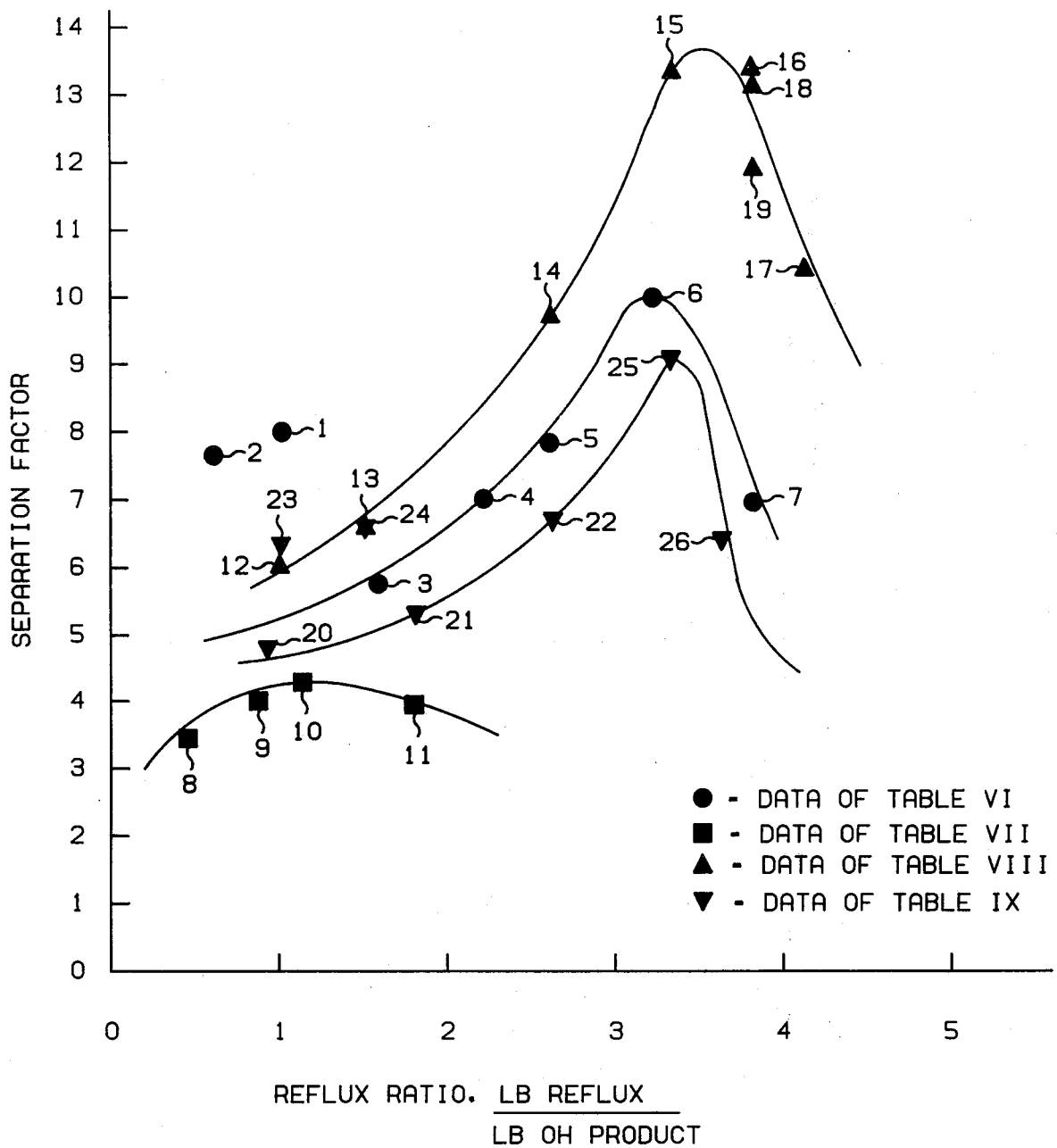
FIG. 5 portrays data from Examples IV and V to show increases in separation efficiencies as reflux ratio is increased up to a maximum or optimum ratio.

The above data are plotted in FIG. 5 with the Run No. shown beside each experimental point. Neglecting Runs 1 and 2, which appear out of line, the data show the characteristic increase in column separating efficiency, plotted as separation factor, as the reflux ratio is increased from about 1.5 to about 3 at which point the efficiency peaks. The broad desirable ratio with this feedstock and separation conditions of temperature, solvent ratios, and the like, appears to be about 2.9–3.2. Use of additional reflux, such as with a reflux ratio of 3.79, beyond the optimum, results in a decrease in efficiency. It is not known at this time why Runs 1 and 2 showed unexpectedly high efficiencies. Since all other runs indicate a decrease in efficiency as the reflux ratio approaches zero, it can only be concluded that Runs 1 and 2 are erroneous. Operation of the column with this system using a reflux ratio greater than about 2 caused two liquid phases to be present in the top of the column and the data and FIG. 5 therefore illustrate the high separation efficiency to be obtained by operating at the optimum reflux ratio of about 3 even through two liquid phases are present.

EXAMPLE V

Another series of tests were made with a different butadiene concentration in the feedstock and a different solvent-to-feed ratio. Data are presented in Table VII below:

TABLE VII

Separation of Butadiene and Butene-1
Solvent: 48 wt. % Sulfolane
48 wt. % Methyl Carbitol
4 wt. % Water

| Run No. | Feed Composition, wt. % Butadiene | Solvent to Feed Ratio, lb/lb | Reflux Ratio, lb. Reflux per lb. OH Product | Separation Factor, SF |
|---|---|---|---|---|
| 8 | 29.9 | 5.5 | 0.45 | 3.51 |
| 9 | 30.1 | 5.5 | 0.85 | 3.97 |
| 10 | 29.7 | 5.5 | 1.14 | 4.53 |
| 11 | 29.9 | 5.5 | 1.75 | 4.02 |

The above data, also plotted in FIG. 5 show a maximum efficiency for a reflux ratio of about 1.2 where two liquid phases were present in the top of the column.

It is to be observed that the optimum reflux ratio of about 1 obtained in Example V differs appreciably from the optimum reflux ratio of about 3.2 obtained in Example IV. This is because of the appreciable difference in feedstock compositions in the two examples. An optimum reflux ratio exists for each set of extractive distillation column operating variables but it will change when one or more of the other variables is changes such as feedstock composition, solvent to feed ratio, the solvent itself, etc.

EXAMPLE VI

In still another series of tests the butadiene-butene-1 system was separated using as solvent a mixture of 58 wt. % sulfolane, 38.5 wt. % methyl carbitol and 3.5 wt. % water. Results are tabulated in Table VIII below:

TABLE VIII

Separation of Butadiene and Butene-1
Solvent: 58 wt. % sulfolane
38.5 wt. % methyl carbitol
3.5 wt. % Water

| Run No. | Feed Composition, wt. % Butadiene | Solvent to Feed Ratio, lb/lb | Reflux Ratio, lb. Reflux per lb. OH Product | Separation Factor, SF |
|---|---|---|---|---|
| 12 | 48.1 | 8.0 | 1.0 | 5.98 |
| 13 | 47.8 | 8.0 | 1.5 | 6.43 |
| 14 | 46.6 | 8.0 | 2.6 | 9.86 |
| 15 | 47.1 | 8.0 | 3.3 | 9.86 |
| 16 | 46.9 | 8.0 | 3.8 | 13.3 |
| 17 | 45.6 | 8.0 | 4.1 | 10.4 |
| 18 | 45.4 | 8.0 | 3.8 | 13.3 |
| 19 | 45.9 | 8.0 | 3.8 | 11.9 |

EXAMPLE VII

Additional tests were made as in Example VI but at a lower solvent-to-feed ratio and the results of Table IX obtained.

TABLE IX

Separation of Butadiene and Butene-1
Solvent: 58 wt. % sulfolane
38.5 wt. % methyl carbitol
3.5 wt. % Water

| Run No. | Feed Composition, wt. % Butadiene | Solvent to Feed Ratio, lb/lb | Reflux Ratio, lb. Reflux per lb. OH Product | Separation Factor, SF |
|---|---|---|---|---|
| 20 | 45.3 | 7.0 | 0.9 | 4.9 |
| 21 | 46.4 | 7.0 | 1.8 | 5.2 |
| 22 | 48.7 | 7.0 | 2.6 | 6.7 |
| 23 | 48.6 | 7.0 | 1.0 | 6.4 |
| 24 | 48.2 | 7.0 | 1.5 | 6.4 |
| 25 | 47.8 | 7.0 | 3.3 | 8.6 |
| 26 | 47.0 | 7.0 | 3.8 | 6.4 |

The data from Table III also are plotted in FIG. 5 and again illustrate the peak in separation efficiency at optimum reflux ratios in the presence of two liquid phases.

The disclosure, including data, illustrate the value and effectiveness of my invention. The examples, the knowledge and background of the field of the invention and general principles of chemistry and other applicable sciences, have formed the bases from which the broad descriptions of the invention including the ranges of conditions and generic groups of operant components have been developed, which have formed the bases for my claims here appended.

What is claimed is:

1. A method of operating an extractive distillation column means at substantially maximum separation efficiencies so as to separate at least one component from a feedstock comprising an admixture of at least two organic components such that the relative volatilities of said components are sufficiently close as to substantially preclude effective separation by fractional distillation, wherein said extractive distillation column means comprises an upper extractive distillative zone and a contiguous lower stripping zone, which process comprises:

feeding said feedstock to said extractive distillative zone of said column means, contacting said feedstock with a lean highly selective solvent in amounts sufficient to provide predetermined ratios of solvent:feedstock effective to substantially change the relative volatilities of said components under extractive distillation conditions, so as to form an overhead vaporous stream of the more volatile of said components and a bottoms stream of the less volatile of said components plus said solvent, separating said bottoms stream into a stream of separated selective solvent and a stream of said less volatile components, recycling said separated selective solvent to said contacting step as said lean highly selective solvent, recycling at least a portion of said stream of less volatile components to the said stripping zone of said column means, to function as stripping vapor therein, condensing at least a portion of said vaporous overhead as a condensed stream, removing the remainder of said overhead as raffinate, and returning at least a portion of said condensed stream as reflux to said extractive distillative zone of said column means in amounts sufficient to provide effective substantially optimum predetermined ratios of reflux:raffinate, such that the said predetermined ratios of solvent:feedstock and reflux:raffinate are effective in combination to provide two immiscible liquid phases only in the upper portion of said extractive distillative zone of said column means, above the point of entry of said feedstock, and to operate said extractive distillation column means at said substantially maximum separation efficiencies, and wherein said two immiscible liquid phases represent a solvent-rich phase and a phase rich in the more volatile feedstock components.

2. A process according to claim 1 of separating aromatic hydrocarbons from a feedstock mixture comprising aromatic hydrocarbons, naphthenes, and paraffinics, which comprises contacting in extractive distillation means said feedstock mixture with a highly selective solvent under conditions of extractive distillation, thereby forming an overhead vaporous stream comprising said paraffinics and naphthenes, and a kettle liquid stream comprising rich solvent and said aromatics, distilling said bottoms liquid stream under fractional distillation separation conditions, thereby separating said bottoms stream into streams comprising an extract aromatics-rich stream comprising said aromatics, and a lean solvent stream, recycling said lean solvent stream to said contacting step as said highly selective solvent, condensing at least a portion of said overhead vaporous stream into a stream of condensed more volatile components, and refluxing at least a portion of said condensed overhead to the upper portion of said extractive distillative means, and removing the remainder of said overhead as a raffinate of said paraffinics and naphthenes.

3. The process according to claim 2 wherein said solvent is sulfolane, optionally further containing about 0.1 to 20 weight percent water.

4. The process of claim 2 wherein said optimum reflux ratio is about 0.5 to 0.7.

5. The process of claim 2 wherein said feedstock is a pyrolysis gasoline fraction derived from catalytic or thermal cracking of a petroleum feed.

6. The process of claim 5 wherein said feedstock mixture comprises the $C_7$ through $C_{10}$ boiling range of said pyrolysis gasoline fraction and further comprises olefinics, said overhead vaporous stream comprises $C_7$–$C_{10}$ paraffins, naphthenes, and olefins, said bottoms liquid stream comprises said aromatics and $nC_9+$ paraffins, and said process of separating further comprises the steps of fractionating said bottoms liquid stream of aromatics and $nC_9+$ paraffins into streams comprising benzene, toluene, xylenes, and a residual stream of $C_9+$ aromatics and paraffinics, and extractively distilling said residual stream of $C_9+$ aromatics and paraffinics, thereby separating $nC_9+$ paraffins from said $C_9+$ aromatics.

7. The process according to claim 1 wherein said admixture to be separated comprises butadiene, butenes, and butane, and said process effectively separates butadiene from said butenes and butanes, and said highly selective solvent is a sulfolane-type solvent, a sulfolene-type solvent, or either of said solvents with 0.1 to 20 weight percent water.

8. The process of claim 7 wherein said selective solvent comprises an admixture of sulfolane, diethylene glycol monomethyl ether, and water in a ratio of about 1:1:0.1, and said reflux ratio is about 2.9–3.2 employing a solvent:feed ratio of about 7 lb.:lb.

9. The process of claim 7 wherein said selective solvent comprises an admixture of sulfolane, diethylene glycol monomethyl ether, and water in a ratio of about 1:10.1, and said reflux ratio is about 1.1–1.2 employing a solvent:feed ratio of about 5.5 lb.:lb.

10. The process of claim 7 wherein said selective solvent comprises an admixture of sulfolane, diethylene glycol monomethyl ether, and water in a ratio of about 1:0.65:0.06, and said reflux ratio is about 3.5–3.8 employing a solvent:feed ratio of about 8 lb.:lb.

11. The process of claim 7 wherein said selective solvent comprises an admixture of sulfolane, diethylene glycol monomethyl ether, and water in a ratio of about 1:0.65:0.06, and said reflux ratio is about 3.2–3.4 employing a solvent:feed ratio of about 7 lb.:lb.

12. The process according to claim 1 wherein said admixture to be separated comprises isoprene, pentanes, and amylenes other than said isoprene, said process effectively separates isoprene from the balance of said admixture, and wherein said highly selective solvent is a sulfolane-type solvent, a sulfolene-type solvent, or either with about 0.1 to 20 weight percent water.

13. The process according to claim 1 wherein said feedstock comprises cyclohexane in admixture with close boiling paraffins including hexanes, said process effectively separates said cyclohexane from said close boiling paraffins, and wherein said highly selective solvent is a sulfolane-type solvent, a sulfolene-type solvent, or either with about 0.1 to 20 weight percent water.

14. The process according to claim 1 wherein said feedstock to be separated is a cracked gasoline fraction containing toluene through $C_{10}$ aromatics, said process effectively separates a high purity aromatics stream comprising toluene through $C_{10}$ aromatics, and wherein said highly selective solvent is a sulfolane-type solvent, a sulfolene-type solvent, or either with about 0.1 to 20 weight percent water.

15. The process according to claim 1 wherein said selective solvent is a sulfolane-type solvent or a sulfolene-type solvent.

16. The process according to claim 15 wherein said solvent is a sulfolane-type solvent of the general formula:

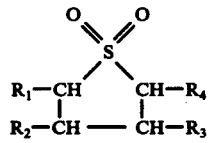

wherein $R_1$, $R_2$, $R_3$, and $R_4$ each is independently selected from the group consisting of hydrogen, alkyl of 1 to 10 carbon atoms, arylalkyl of up to 12 carbon atoms, and alkoxy of up to 8 carbon atoms.

17. The process of claim 16 wherein said sulfolane-type solvent is employed in admixture with at least one cosolvent selected from the group consisting of water, glycols, glycol ethers, alcohols, and ketones.

18. The process of claim 17 wherein said sulfolane-type solvent is solfolane, and said sulfolane is employed in admixture with a said ketone comprising acetone, and optionally further with a minor amount of water.

19. The process according to claim 15 wherein said solvent is a sulfolene and is 2-sulfolene or 3-sulfolene.

20. The process according to claim 15 wherein said solvent further comprises a minor effective amount of water in the range of about 0.1 to 20 weight percent relative to the total of solvent plus water.

21. The process of claim 20 wherein said minor amount of water represents about 0.5 to 1 weight percent.

* * * * *

UNITED STATES PATENT AND TRADEMARK OFFICE
CERTIFICATE OF CORRECTION

PATENT NO. : 4,053,369
DATED : October 11, 1977
INVENTOR(S) : Martin R. Cines

It is certified that error appears in the above-identified patent and that said Letters Patent are hereby corrected as shown below:

Column 17, claim 9, line 6, delete "1:10.1," and insert therefore --- 1:1:0.1, ---.

Signed and Sealed this

Sixteenth Day of May 1978

[SEAL]

Attest:

RUTH C. MASON
Attesting Officer

LUTRELLE F. PARKER
Acting Commissioner of Patents and Trademarks